United States Patent
Ye

(10) Patent No.: US 11,631,490 B2
(45) Date of Patent: Apr. 18, 2023

(54) MEDICAL IMAGE DISPLAY DEVICE, METHOD, AND PROGRAM FOR MANAGING THE DISPLAY OF ABNORMALITY DETECTION RESULTS

(71) Applicant: FUJIFILM Corporation, Tokyo (JP)

(72) Inventor: Mon Aung Ye, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/192,841

(22) Filed: Mar. 4, 2021

(65) Prior Publication Data

US 2021/0210196 A1 Jul. 8, 2021

Related U.S. Application Data

(63) Continuation of application No. PCT/JP2019/019583, filed on May 16, 2019.

(30) Foreign Application Priority Data

Sep. 25, 2018 (JP) .............................. JP2018-178490

(51) Int. Cl.
*G16H 30/40* (2018.01)
*A61B 6/00* (2006.01)
*G09G 5/14* (2006.01)

(52) U.S. Cl.
CPC ............. *G16H 30/40* (2018.01); *A61B 6/463* (2013.01); *G09G 5/14* (2013.01); *G09G 2380/08* (2013.01)

(58) Field of Classification Search
None
See application file for complete search history.

(56) References Cited

U.S. PATENT DOCUMENTS

| 7,577,282 | B2 | 8/2009 | Gkanatsios et al. |
| 8,867,807 | B1 * | 10/2014 | Fram ................. G06T 7/20 382/128 |
| 9,095,306 | B2 | 8/2015 | Gkanatsios et al. |
| 9,396,534 | B2 | 7/2016 | Kutsuna et al. |
| 9,460,508 | B2 | 10/2016 | Gkanatsios et al. |
| 10,108,329 | B2 | 10/2018 | Gkanatsios et al. |
| 10,452,252 | B2 | 10/2019 | Gkanatsios et al. |

(Continued)

FOREIGN PATENT DOCUMENTS

| JP | H10225441 | 8/1998 |
| JP | 2000311212 | 11/2000 |

(Continued)

OTHER PUBLICATIONS

"International Search Report (Form PCT/ISA/210) of PCT/JP2019/019583," dated Aug. 13, 2019, with English translation thereof, pp. 1-6.

(Continued)

*Primary Examiner* — Patrick F Valdez
(74) *Attorney, Agent, or Firm* — JCIPRNET

(57) ABSTRACT

A first display controller displays a plurality of medical images in which a detection result of at least one abnormal part is added to at least one medical image, on a display. A second display controller displays a total number of detection results on the display. A third display controller displays reference information representing a reference state of the detection result on the display.

17 Claims, 14 Drawing Sheets

(56) References Cited

U.S. PATENT DOCUMENTS

| | | | | | |
|---|---|---|---|---|---|
| 2002/0158875 | A1* | 10/2002 | Yamada | .................... | G06T 5/00 |
| | | | | | 345/440 |
| 2006/0093198 | A1* | 5/2006 | Fram | ...................... | A61B 6/464 |
| | | | | | 382/128 |
| 2007/0052685 | A1* | 3/2007 | Wakai | .................... | G06F 9/451 |
| | | | | | 715/764 |
| 2007/0198130 | A1* | 8/2007 | Wang | .................... | G16H 80/00 |
| | | | | | 700/259 |
| 2008/0039152 | A1* | 2/2008 | Arisawa | ............... | H04M 19/04 |
| | | | | | 455/567 |
| 2010/0057496 | A1* | 3/2010 | Fors | ....................... | G06Q 10/00 |
| | | | | | 705/3 |
| 2011/0123087 | A1* | 5/2011 | Nie | .......................... | G06T 7/62 |
| | | | | | 345/629 |
| 2016/0314589 | A1* | 10/2016 | Nagao | .................... | G16H 30/20 |

FOREIGN PATENT DOCUMENTS

| | | |
|---|---|---|
| JP | 2011110429 | 6/2011 |
| JP | 5702041 | 4/2015 |
| JP | 2015198928 | 11/2015 |
| JP | 2018142072 | 9/2018 |

OTHER PUBLICATIONS

"Written Opinion of the International Searching Authority (Form PCT/ISA/237) of PCT/JP2019/019583," dated Aug. 13, 2019, with English translation thereof, pp. 1-7.

* cited by examiner

| PATIENT NAME | ORDER NUMBER | PATIENT ID | MODALITY | NUMBER OF IMAGES |
|---|---|---|---|---|
| Y S | 20180810001 | AB1234 | CT | 246 |
| N I | 20180811022 | AC5678 | MRI | 246 |
| R S | 20180825021 | AD1372 | CT | 54 |
| N F | 20180825023 | AE1965 | CT | 455 |

L0

MEDICAL IMAGE DISPLAY DEVICE, METHOD, AND PROGRAM FOR MANAGING THE DISPLAY OF ABNORMALITY DETECTION RESULTS

CROSS REFERENCE TO RELATED APPLICATIONS

The present application is a Continuation of PCT International Application No. PCT/JP2019/019583 filed on May 16, 2019, which claims priority under 35 U.S.C. § 119(a) to Japanese Patent Application No. 2018-178490 filed on Sep. 25, 2018. Each of the above applications is hereby expressly incorporated by reference, in its entirety, into the present application.

BACKGROUND

Technical Field

The present disclosure relates to a medical image display device, a medical image display method, and a medical image display program which display a plurality of medical images.

Related Art

With higher performance such as multi-slice support and higher speed of image capturing devices (modality) such as computed tomography (CT) devices or magnetic resonance imaging (MM) devices, it is possible to acquire a three-dimensional image consisting of a plurality of tomographic images obtained by imaging a plurality of parts of a patient as a subject in one imaging series. Accordingly, since it is not necessary for the patient to be imaged multiple times for each part, and the entire imaging time is shortened, the burden on the patient is reduced.

In a case where the three-dimensional image acquired by such a CT device or MM device is interpreted on an image viewer, tomographic images each representing a two-dimensional tomographic plane are observed by being switched in order and displayed on the image viewer. In a case of performing interpretation, comparative interpretation of a plurality of three-dimensional images is performed in many cases. For example, in a case where a plurality of imaging series are included in one inspection, tomographic images of the plurality of imaging series are displayed in parallel on the image viewer, and comparative interpretation of the tomographic images of each imaging series is performed.

Further, the medical image is analyzed by a computer-aided diagnosis (CAD) using a discriminator in which learning has been performed by deep learning or the like to extract a region, a position, a volume, and the like of an abnormal part such as a lesion included in the medical image, and the region, the position, the volume, and the like are acquired as an analysis result. In this manner, a CAD detection result generated by an analysis process using the CAD is saved in a database in association with inspection information such as the patient name, the gender, the age, and the modality that has acquired the medical image, and is supplied to a diagnosis. In this case, in the three-dimensional image, a mark or the like for specifying an abnormal part is added to the tomographic image of the tomographic plane where the abnormal part is detected (for example, refer to JP5702041B). The mark may be directly added to the tomographic image, or the mark may be saved as a detection result image separate from the tomographic image, and the detection result image may be superimposed and displayed on the tomographic image where an abnormality is detected when the tomographic image is displayed on the image viewer. A radiologist performs interpretation of the medical image while referring to the detection result of such a CAD, and creates an interpretation report.

On the other hand, various methods for supporting the interpretation of medical images have been proposed. For example, JP2015-198928A has proposed a method of generating an interpretation determination table in which images corresponding to parts and local structures where the interpretation is required are listed when a plurality of tomographic images constituting the three-dimensional image are displayed, and determining whether each tomographic image has been interpreted. JP1998-225441A (JP-H10-225441A) has proposed a method of displaying information that can identify the number of images and whether the image has been interpreted or not when a plurality of medical images are displayed. Further, JP2000-311212A has proposed a method of inputting a plurality of different medical images and ancillary information of these medical images, determining whether the plurality of medical images have been interpreted or not from the ancillary information, and writing, in the ancillary information, the number of times a CAD target image is displayed (number of references) from the start of interpretation in the accompanying information.

However, in recent years, with higher resolution modality that acquires the three-dimensional image, the interval of the tomographic planes of the tomographic images constituting the three-dimensional image is reduced, and as a result, the number of acquired tomographic images is increased. During performing the interpretation, it is necessary to check the presence or absence of an abnormality by displaying all of the tomographic images, but in a case where the number of tomographic images is increased, a situation may occur in which the radiologist does not display all of the tomographic images. In such a situation, especially in a case where the tomographic image including the detection result of the abnormal part of the CAD is not displayed, the abnormality may be overlooked.

SUMMARY OF THE INVENTION

The present disclosure is made in view of such circumstances, and an object thereof is to prevent overlooking an abnormality in a case where a plurality of medical images including a detection result of an abnormal part are displayed.

A medical image display device according to an aspect of the present disclosure includes a first display controller that displays a plurality of medical images in which a detection result of at least one abnormal part is added to at least one medical image, on a display unit; a second display controller that displays a total number of detection results on the display unit; and a third display controller that displays reference information representing a reference state of the detection result on the display unit.

In the medical image display device according to the aspect of the present disclosure, the reference information may be the number of referenced detection results among the detection results.

In the medical image display device according to the aspect of the present disclosure, the reference information may be the number of unreferenced detection results among the detection results.

The medical image display device according to the aspect of the present disclosure may further include a notification unit that, in a case where there is an unreferenced detection result at the time of ending display of the plurality of medical images, gives a notification that there is the unreferenced detection result.

The medical image display device according to the aspect of the present disclosure may further include a first switching unit that switches between display and non-display of the detection result in a case where information on the detection result is present separately from the plurality of medical images, or in a case where there are a plurality of medical images not including the detection result, which correspond to the plurality of medical images including the detection result.

The medical image display device according to the aspect of the present disclosure may further include a second switching unit that switches between display and non-display of at least one of the total number or the reference information.

In the medical image display device according to the aspect of the present disclosure, the first display controller may display only the medical image to which the detection result is added.

In the medical image display device according to the aspect of the present disclosure, in a case where the detection result is added to a plurality of medical images, the first display controller may sequentially display the medical images to which the detection result is added.

In the medical image display device according to the aspect of the present disclosure, in a case where the detection result is added to a plurality of medical images, the first display controller may display the medical images to which the detection result is added, in parallel.

In the medical image display device according to the aspect of the present disclosure, the plurality of medical images may be medical images included in at least one imaging series among a plurality of imaging series for one inspection.

The "at least one imaging series among a plurality of imaging series" may be one imaging series for one inspection, or may be two or more imaging series or all imaging series.

A medical image display method according to another aspect of the present disclosure includes displaying a plurality of medical images in which a detection result of at least one abnormal part is added to at least one medical image, on a display unit; displaying a total number of detection results on the display unit; and displaying reference information representing a reference state of the detection result on the display unit.

A medical image display program for causing a computer to execute the medical image display method according to the aspect of the present disclosure may be provided.

A medical image display device according to another aspect of the present disclosure includes a memory that stores a command for execution of a computer, and a processor configured to execute the stored command, in which the processor executes processing of displaying a plurality of medical images in which a detection result of at least one abnormal part is added to at least one medical image, on a display unit, displaying a total number of detection results on the display unit, and displaying reference information representing a reference state of the detection result on the display unit.

According to the present disclosure, in a case where a plurality of medical images including a detection result of an abnormal part are displayed, it is possible to prevent overlooking the abnormality.

DETAILED DESCRIPTION

Figure 1:
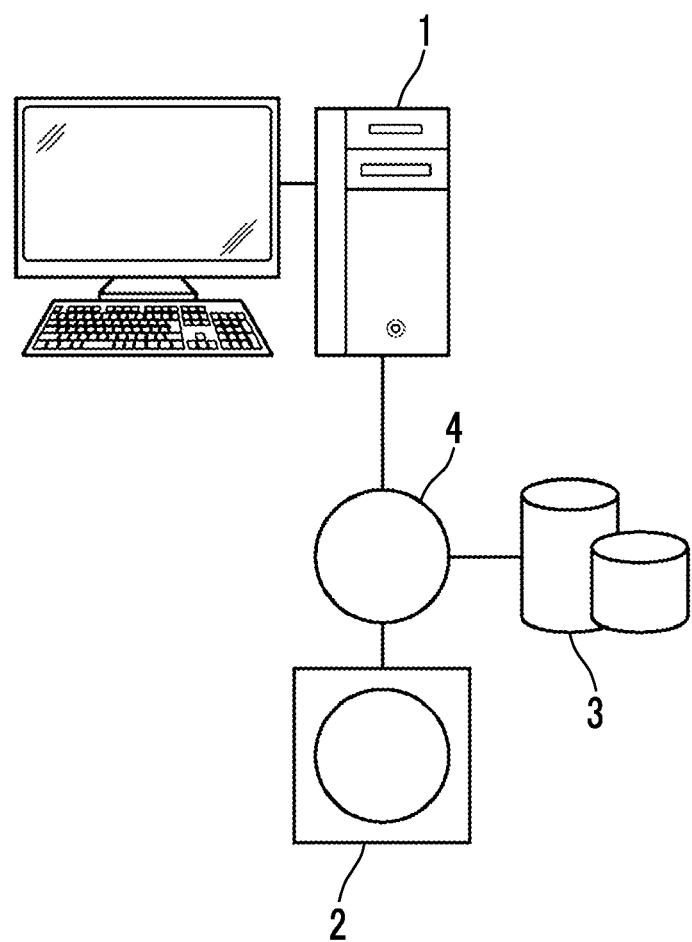
FIG. 1 is a hardware configuration diagram illustrating an outline of a diagnosis support system to which a medical image display device according to an embodiment of the present disclosure is applied.

Hereinafter, embodiments of the present disclosure will be described in detail with reference to the drawings. FIG. 1 is a hardware configuration diagram illustrating an outline of a diagnosis support system to which a medical image display device according to an embodiment of the present disclosure is applied. As illustrated in FIG. 1, in the diagnosis support system, a medical image display device 1 according to the embodiment, a three-dimensional image capturing device 2, and an image storage server 3 are connected via a network 4 in a communicable state.

The three-dimensional image capturing device 2 is a device that images a part as a diagnosis target of a subject to generate a three-dimensional image representing the part, and specifically, is a CT device, an MRI device, a positron emission tomography (PET) device, or the like. In the embodiment, at least one imaging series is included in one inspection on the subject. In the imaging series, the type of image (CT image or MRI image), an imaging range (chest, abdomen, and the like), and the like are determined, and at least one image is acquired in each of the imaging series. For example, one imaging series includes a three-dimensional image consisting of a plurality of tomographic images acquired by the three-dimensional image capturing device 2 imaging the target part of the subject.

The image storage server 3 is a computer that saves and manages various kinds of data, and comprises a large-capacity external storage device and software for database management. The image storage server 3 performs communication with other devices via the network 4 in a wired or wireless manner, and transmits and receives various kinds of image data. Specifically, the image data such as the three-dimensional image generated by the three-dimensional image capturing device 2 is acquired via the network, and is saved and managed in a recording medium such as a large-capacity external storage device. The image data storage format and the communication between the devices via the network 4 are based on a protocol such as Digital Imaging and Communications in Medicine (DICOM). In the embodiment, it is assumed that in the image storage server 3, images of a plurality of imaging series are stored for each inspection. In the embodiment, it is assumed that in the image storage server 3, information on the inspection for which the saved images are acquired is stored as an inspection list. The inspection list will be described later.

The medical image display device 1 is obtained by installing a medical image display program of the embodiment in one computer. The computer may be a workstation or a personal computer that a doctor performing a diagnosis operates directly, or a server computer connected to the workstation or personal computer via a network. The medical image display program is distributed by being recorded on a recording medium such as a digital versatile disc (DVD) or a compact disc read only memory (CD-ROM), and is installed to a computer from the recording medium. Otherwise, the medical image display program may be stored in a storage device of a server computer connected to a network or in a network storage in a state of being accessible from the outside, and may be downloaded and installed in a computer that the doctor uses, in response to a request.

Figure 2:
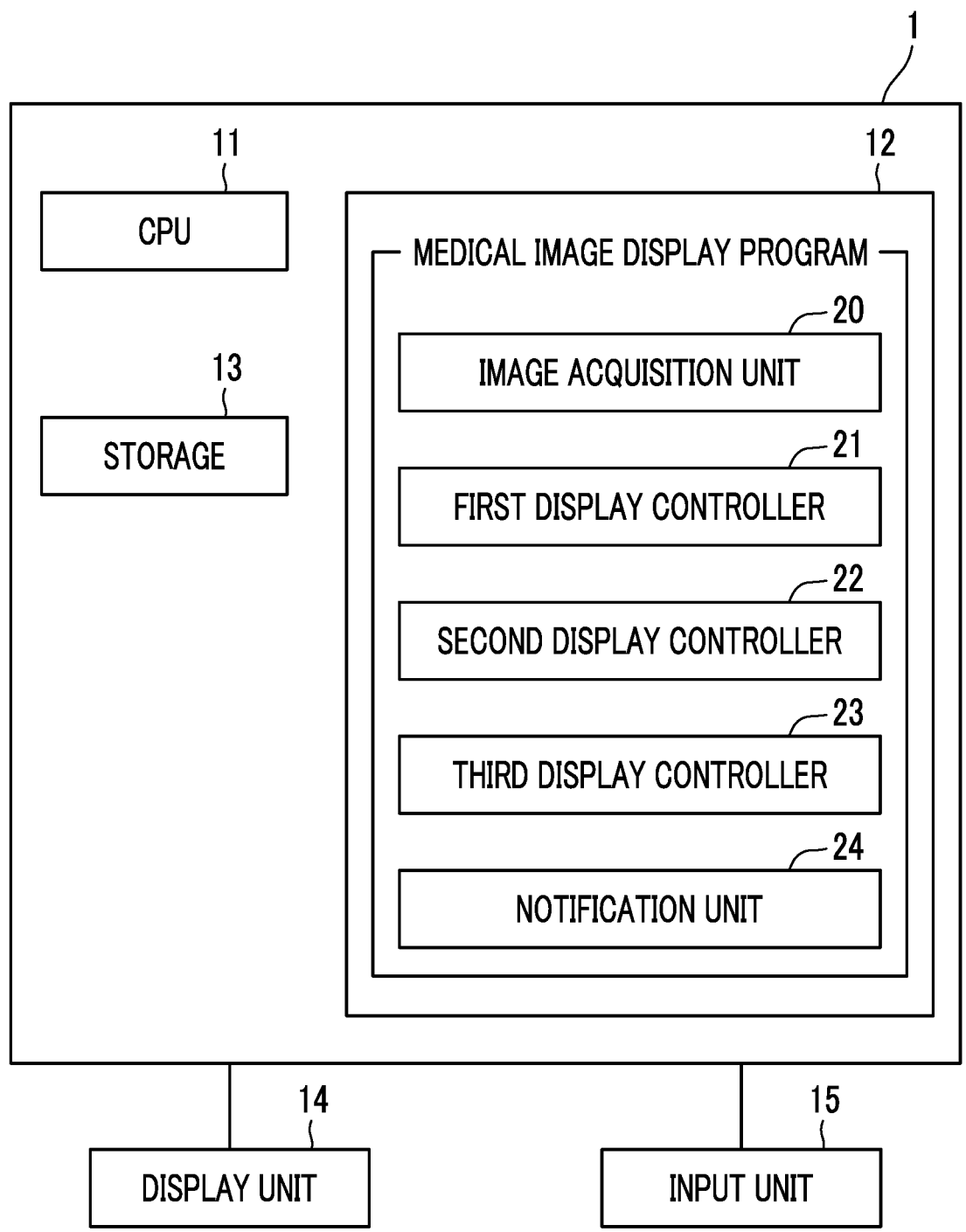
FIG. 2 is a schematic block diagram illustrating a configuration of the medical image display device according to the embodiment.

FIG. 2 is a diagram illustrating a schematic configuration of the medical image display device realized by installing the medical image display program in a computer. As illustrated in FIG. 2, the medical image display device 1 comprises a central processing unit (CPU) 11, a memory 12, and a storage 13 as a standard computer configuration. In addition, a display unit 14 such as a liquid crystal display, and an input unit 15 such as a keyboard and a mouse are connected to the medical image display device 1. The input unit 15 corresponds to a first switching unit and a second switching unit.

The storage 13 consists of a storage device such as a hard disk drive or a solid state drive (SSD). In the storage 13, various kinds of information, including the images of the subject and information required for the process, which are acquired from the image storage server 3 via the network 4 are stored.

In the memory 12, the medical image display program is stored. The medical image display program defines, as the process executed by the CPU 11, an image acquisition process of acquiring a plurality of medical images in which a detection result of at least one abnormal part is added to at least one medical image, a first display control process of displaying the plurality of medical images to which the detection result is added on the display unit 14, a second display control process of displaying a total number of detection results on the display unit 14, a third display control process of displaying reference information representing a reference state of the detection result on the display unit 14, and a notification process of performing notification that there is an unreferenced detection result in a case where there is an unreferenced detection result at the time of ending the display of the medical images.

With the CPU 11 executing those processes according to the program, the computer functions as an image acquisition unit 20, a first display controller 21, a second display controller 22, a third display controller 23, and a notification unit 24. Hereinafter, the processes performed by the image acquisition unit 20, the first display controller 21, the second display controller 22, the third display controller 23, and the notification unit 24 will be described in detail. In the following description, a basic display control process in the medical image display device 1 will be described as being performed by the first display controller 21, but may be performed by the second display controller 22 or the third display controller 23.

Figure 3:
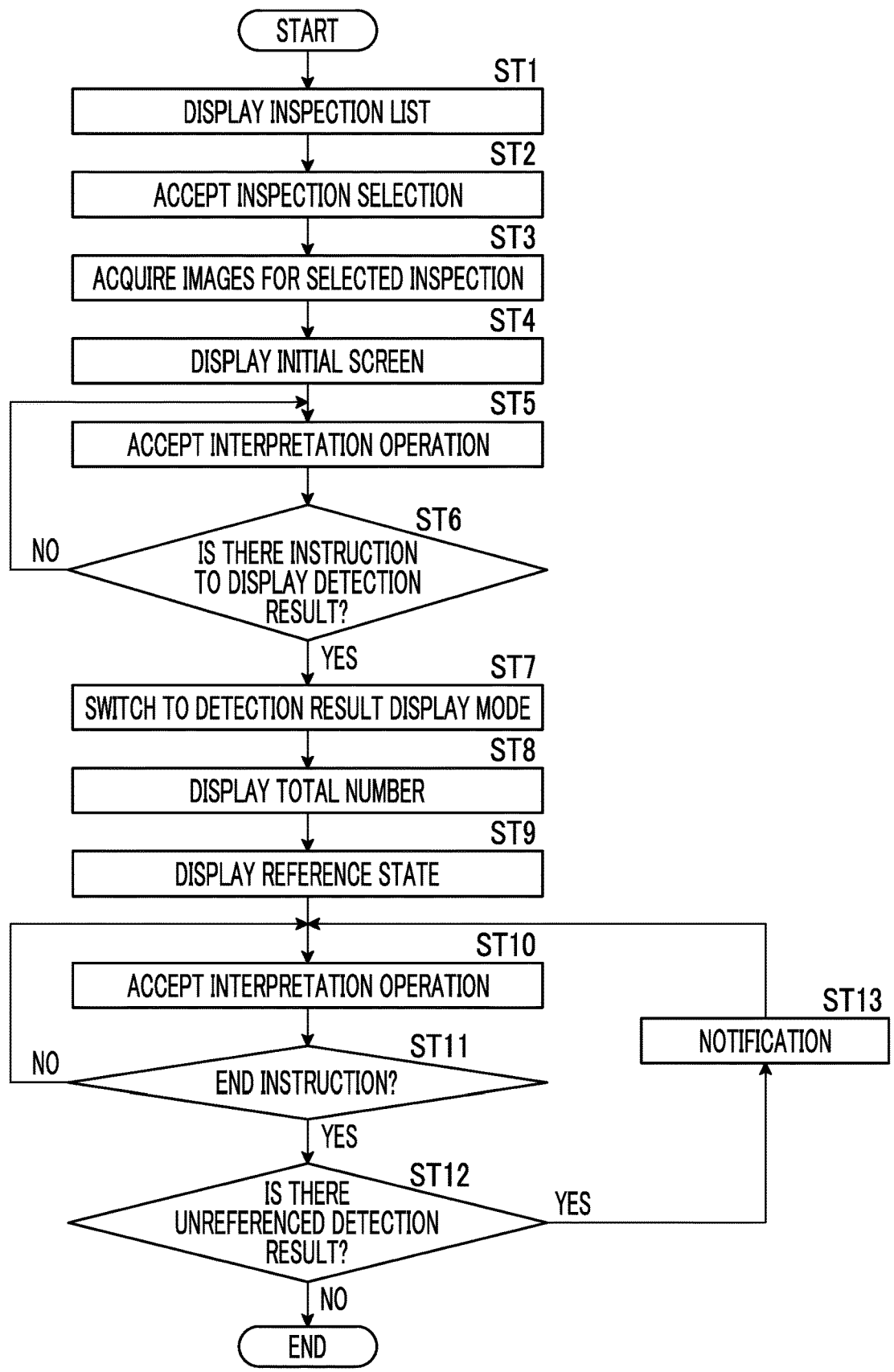
FIG. 3 is a flowchart illustrating a process performed in the embodiment.
Figures 4, 5:
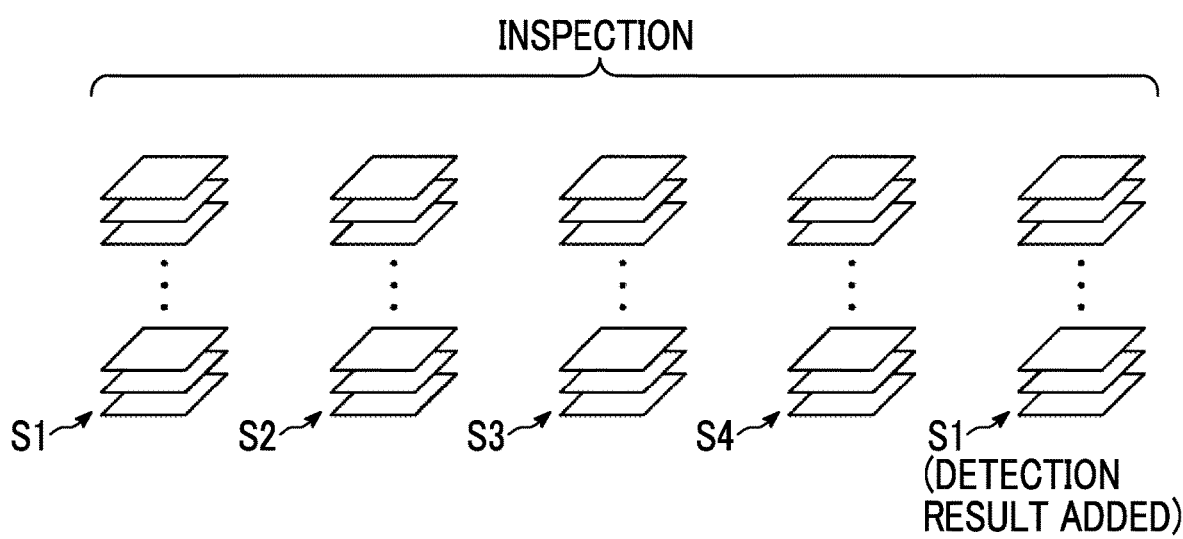
FIG. 4 is a diagram illustrating an inspection list.
FIG. 5 is a diagram for describing imaging series.

FIG. 3 is a flowchart illustrating a process performed in the embodiment. In a case where an instruction to display the inspection list is input from the input unit 15 by the operator, the image acquisition unit 20 acquires the inspection list from the image storage server 3, and the first display controller 21 displays the inspection list on the display unit 14 (Step ST1). FIG. 4 is a diagram illustrating the inspection list. As illustrated in FIG. 4, in an inspection list LO, the patient name, the order number, the patient ID, the modality used in the inspection, the number of images, and the like are included.

First, the operator selects an inspection for performing interpretation from the inspection list LO displayed on the display unit 14. Thus, the first display controller 21 accepts the selection of the inspection by the input unit 15 (Step ST2). In a case where the inspection is selected, the image acquisition unit 20 acquires images for the selected inspection from the image storage server 3 (Step ST3).

FIG. 5 is a diagram illustrating an example of imaging series in one inspection. In one inspection illustrated in FIG. 5, four imaging series S1 to S4 and an imaging series obtained by adding the detection result to the imaging series S1 are included. Each of the five imaging series includes a plurality of tomographic images. Accordingly, one imaging series includes one three-dimensional image. Here, in the embodiment, it is assumed that an analysis process using the CAD is performed on the imaging series S1. Via the analysis process using the CAD, information on a center position of an abnormal part and a diameter of the abnormal part in the tomographic image in which the abnormal part is included is acquired as the detection result. In the embodiment, the detection result is added to the position of the abnormal part in the tomographic image in which the abnormal part is detected, among the plurality of tomographic images included in the imaging series S1, and the imaging series S1 to which the detection result is added is generated in advance, and is included in the inspection. In the embodiment, it is assumed that the detection result is a mark which will be described later. In FIG. 5, the imaging series to which the detection result is added is illustrated as "S1 (detection result added)".

In a case where images for the selected inspection are acquired, the first display controller 21 displays an initial screen of an image viewer on the display unit 14 (Step ST4).

Figure 6:
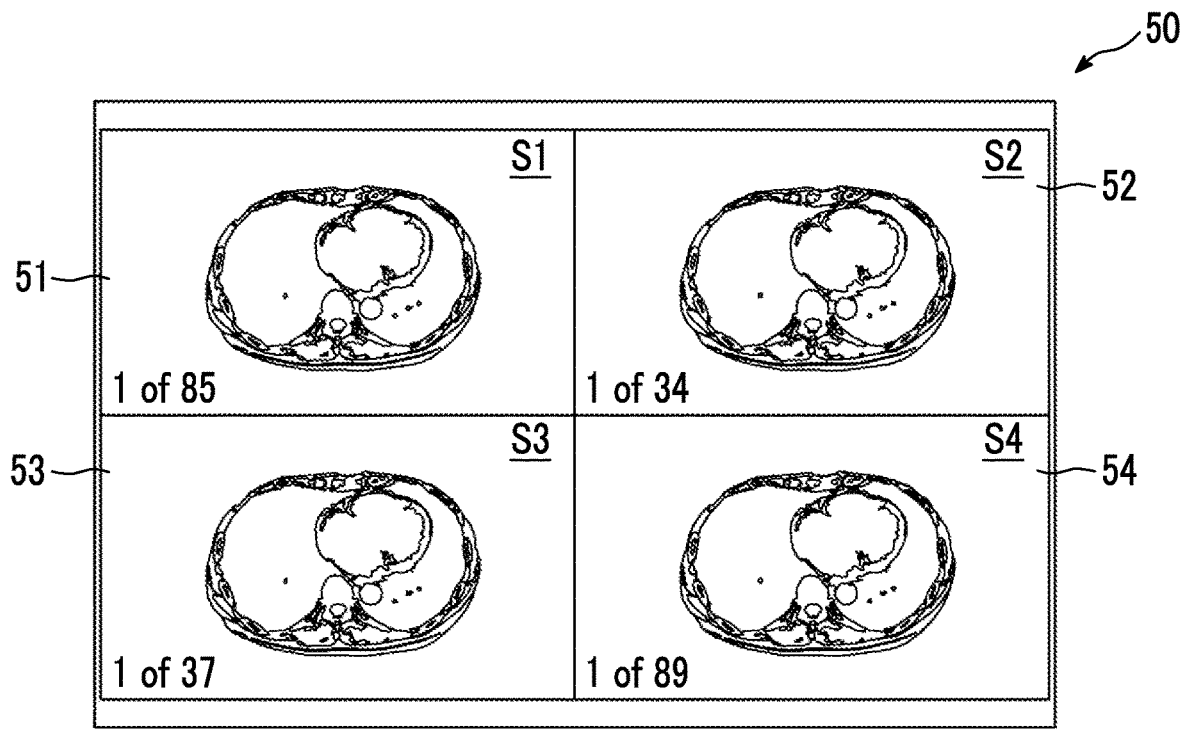
FIG. 6 is a diagram illustrating an initial screen.

FIG. 6 is a diagram illustrating the initial screen of the image viewer. In the embodiment, the image viewer can switch between a detection result non-display mode in which the detection result of the CAD is not displayed, and a detection result display mode in which the detection result of the CAD is displayed. It is assumed that the detection result non-display mode is set at the time of displaying an initial screen 50.

As illustrated in FIG. 6, the initial screen 50 has four image display areas 51 to 54, and leading images of the imaging series S1 to S4 are respectively displayed in the image display areas 51 to 54. The leading image is a tomographic image of a position closest to the head, for example, in a case where the tomographic images included in the imaging series S1 to S4 are images of the axial cross section, but is not limited thereto. For example, the tomographic image of a position closest to the leg may be the leading image. In addition, page information representing the page of the tomographic image being displayed for the total number of tomographic images of each of the imaging series S1 to S4 is displayed in the lower left corner of each of the image display areas 51 to 54. For example, since the total number of tomographic images of the imaging series S1 is 85, "1 of 85", representing that the tomographic image being displayed is the first tomographic image among the 85 tomographic images, is displayed as the page information in the lower left corner of the image display area 51 where the tomographic images of the imaging series S1 are displayed.

The first display controller 21 accepts an operation for the interpretation of the tomographic image by the operator (Step ST5). The operator operates the input unit 15 so that the tomographic images of the imaging series S1 to S4 respectively displayed in the image display areas 51 to 54 are sequentially displayed by scrolling. In this case, the tomographic images of the corresponding tomographic plane of the imaging series S1 to S4 may be linked and sequentially displayed, and the tomographic images of different tomographic planes may be sequentially displayed respectively in the image display areas 51 to 54. Whether to link the tomographic images or not may be switched by an instruction from the input unit 15. Accordingly, the operator can interpret the tomographic images included in each of the imaging series S1 to S4.

Figure 7:
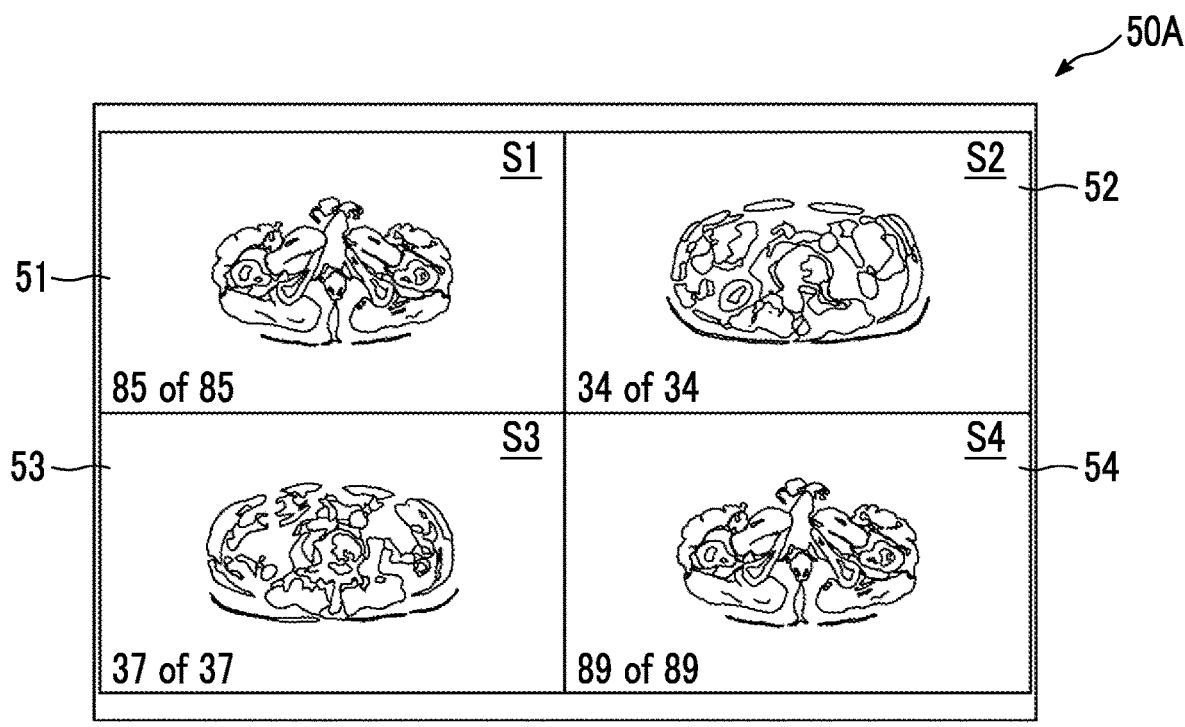
FIG. 7 is a diagram illustrating a display screen after all of tomographic images are interpreted.

FIG. 7 is a diagram illustrating a display screen after all of the tomographic images in the imaging series S1 to S4 are interpreted. On a display screen 50A illustrated in FIG. 7, on the page of the tomographic image being displayed, the page information displayed in the lower left corner of each of the image display areas 51 to 54 matches the total number of tomographic images of each of the imaging series S1 to S4. For example, since the total number of tomographic images of the imaging series S1 is 85, "85 of 85", representing that the tomographic image being displayed is the last tomographic image (that is, 85th) among the 85 tomographic images, is displayed as the page information in the lower left corner of the image display area 51 where the tomographic images of the imaging series S1 are displayed. After all of the images of each of the imaging series S1 to S4 are interpreted, the operator gives an instruction using the input unit 15 to cause the screen to return to the initial screen 50. In this case, the first display controller 21 causes the display of the image viewer to return to the initial screen 50 according to the instruction from the input unit 15.

The operator can give an instruction to display the detection result during the interpretation, using the input unit 15. Therefore, the first display controller 21 determines whether there is an instruction to display the detection result from the input unit 15 (Step ST6). In a case where the determination in Step ST6 is negative, the process returns to Step ST5. In a case where the determination in Step ST6 is affirmative, the first display controller 21 switches the image viewer to the detection result display mode (Step ST7). Accordingly, in the image display area 51, the leading image of the tomographic images of the imaging series 51 to which the detection result is added is displayed. In addition, the second display controller 22 displays the total number of detection results in the imaging series S1 on the display unit 14 (Step ST8), and the third display controller 23 displays the reference information representing the reference state of the detection result on the display unit 14 (Step ST9). In the embodiment, it is assumed that the reference information is the number of detection results that have been referenced.

Figure 8:
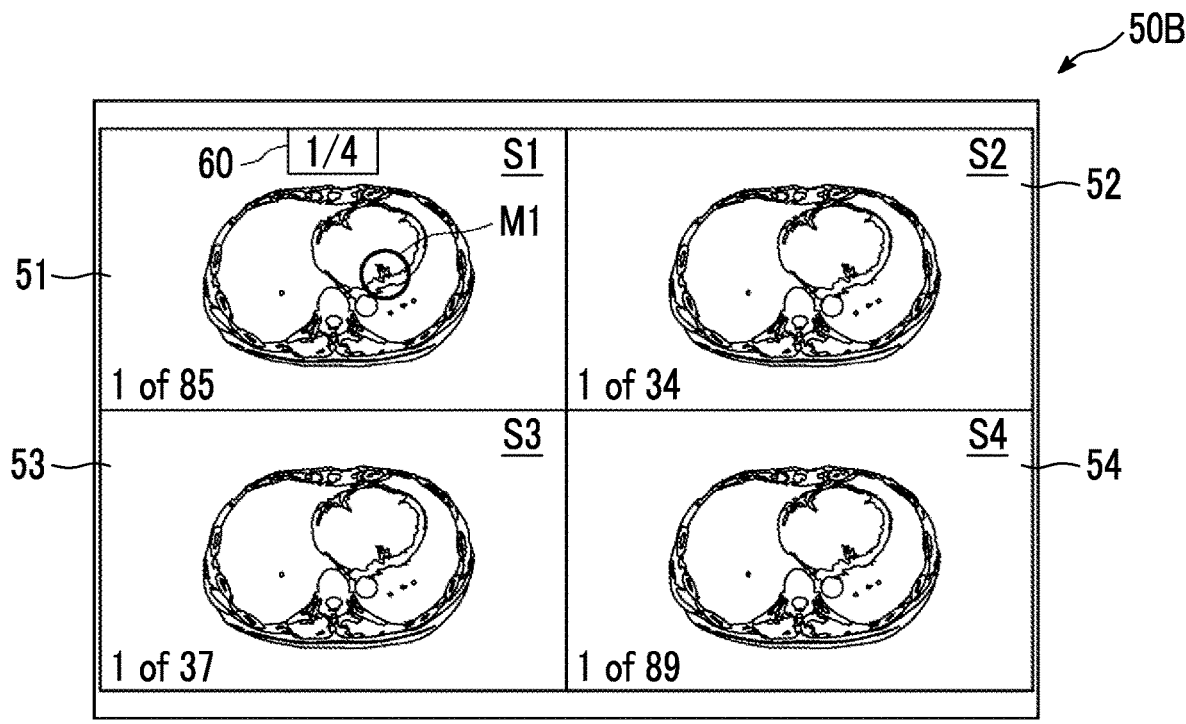
FIG. 8 is a diagram illustrating a display screen in a detection result display mode.

FIG. 8 is a diagram illustrating a display screen in the detection result display mode. As illustrated in FIG. 8, on a display screen 50B in the detection result display mode, the leading image of the imaging series S1 to which the detection result is added is displayed in the image display area 51. The same leading images as those on the initial screen 50 are displayed in the image display areas 52 to 54 of the imaging series S2 to S4 in which the detection result is not included. A circular mark M1 representing the detection result is added to the leading image of the imaging series S1. As the detection result, any symbol, such as an arrow, can be used instead of the circular mark M1.

In the image display area 51, a state display area 60 displaying the total number of detection results included in the imaging series S1 and the reference state of the detection result is displayed. As illustrated in FIG. 8, "1/4" is displayed in the state display area 60. This indicates that the total number of detection results is 4 and the number of referenced detection results is 1. In FIG. 8, the mark M1 representing the detection result is added to the leading image. Therefore, at the stage of switching to the detection result display mode, the first detection result among four detection results is referenced so that "1/4" is displayed in the state display area 60. In a case where the detection result is not added to the leading image, "0/4" is displayed in the state display area 60.

The first display controller 21 accepts an operation for the interpretation of the displayed image (Step ST10). Specifically, similar to the process of Step ST5, the operator operates the input unit 15 so that the images of the imaging series S1 to S4 respectively displayed in the image display areas 51 to 54 are sequentially displayed by scrolling. In this case, the tomographic images of the corresponding tomographic plane of the imaging series S1 to S4 may be linked and sequentially displayed, and the tomographic images of different tomographic planes may be sequentially displayed respectively in the image display areas 51 to 54. Accordingly, in the detection result display mode, the operator can interpret all of the tomographic images of each of the imaging series S1 to S4.

Figure 9:
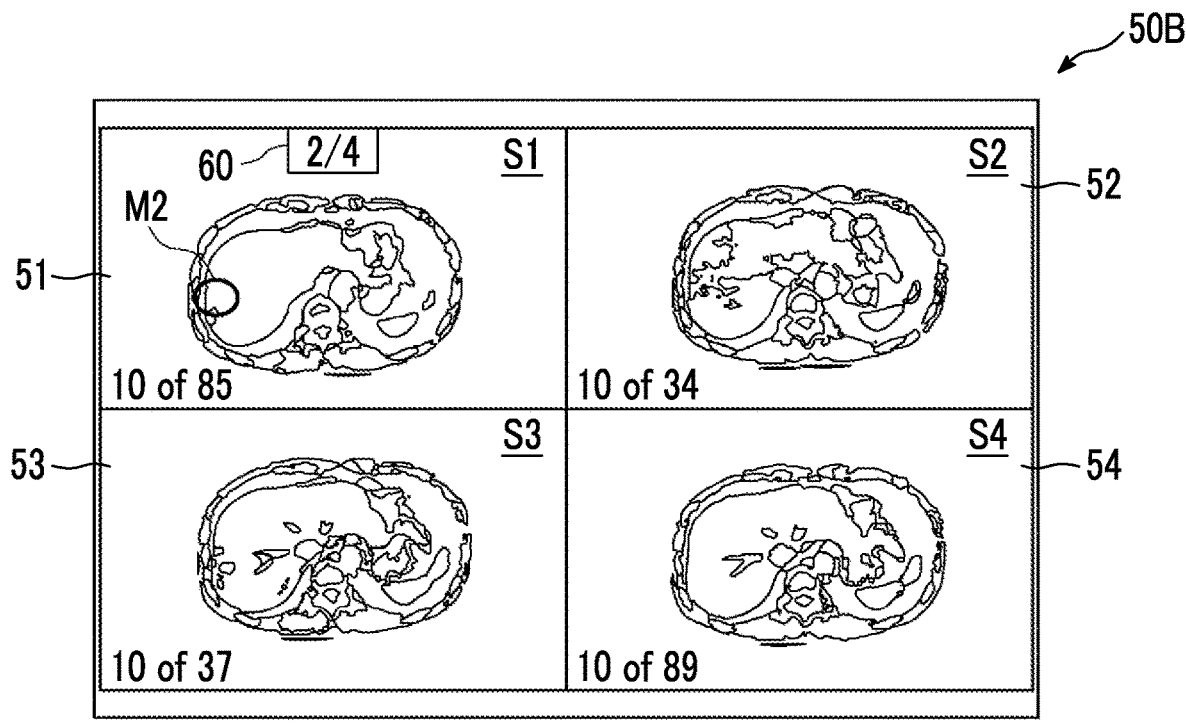
FIG. 9 is a diagram illustrating a display screen in a detection result display mode.

In a case where the interpretation progresses in the detection result display mode and the tomographic image including the detection result is displayed, the reference information in the state display area 60 is changed. For example, as illustrated in FIG. 9, in a case where a mark M2 representing the second detection result is included in the image displayed in the image display area 51, the number of referenced detection results is 2, and as a result, "2/4" is displayed in the state display area 60.

The operator can give an instruction to end the display of the medical image during the interpretation, using the input unit 15. Therefore, the first display controller 21 determines whether there is an end instruction of the display from the input unit 15 (Step ST11). In a case where the determination in Step ST11 is negative, the process returns to Step ST10. In a case where the determination in Step ST11 is affirmative, the notification unit 24 determines whether there is an unreferenced detection result (Step ST12). For example, in the embodiment, it is determined whether all of the four detection results included in the imaging series S1 are referenced.

Figure 10:
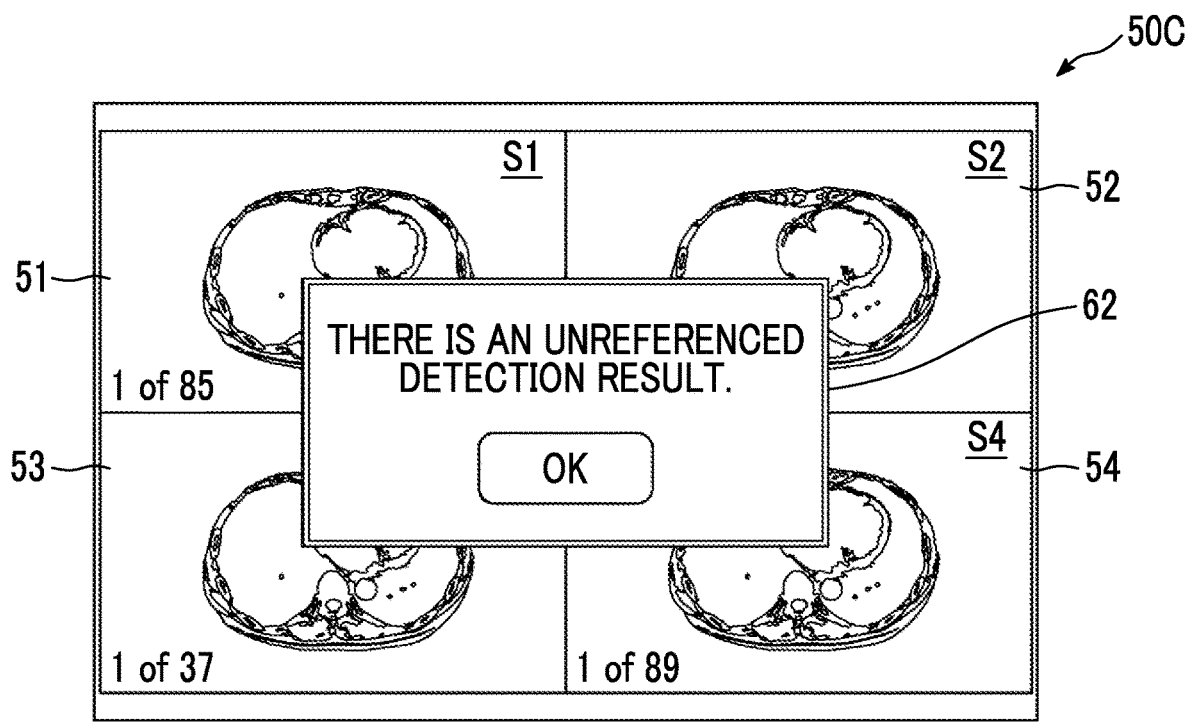
FIG. 10 is a diagram illustrating a notification screen.

In a case where the determination in Step ST12 is affirmative, the notification unit 24 performs notification that there is an unreferenced detection result (Step ST13) in order to cause the operator to reference all of the detection results. Specifically, the notification unit 24 displays a notification screen performing the notification that there is an unreferenced detection result on the display unit 14. FIG. 10 is a diagram illustrating the notification screen. A notification screen 50C illustrated in FIG. 10 includes a notification area 62. In the notification area 62, "There is an unreferenced detection result." is displayed. In a case where an OK button in the notification area 62 is pressed, the process proceeds to Step ST10, and the interpretation is continuously performed. In a case where the determination in Step ST12 is negative, all of the detection results are referenced so that the process is ended. Instead of or in addition to the display of the notification screen 50C, notification by sound may be performed.

In this manner, according to the embodiment, the plurality of tomographic images to which the detection result of the abnormal part are added are displayed on the display unit 14. In this case, the reference information on the total number of detection results and the reference state of the detection result is displayed on the display unit 14. Therefore, an observer (that is, the operator) of the displayed medical image can recognize the total number of detection results and the reference state of the detection result, and can recognize whether there is an unreferenced detection result from the total number of detection results and the reference state of the detection result. Accordingly, according to the embodiment, in a case where the plurality of medical images including the detection result of the abnormal part are displayed, it is possible to prevent overlooking the detection result, and as a result, it is possible to prevent overlooking the abnormality.

Particularly, since the notification that there is an unreferenced detection result is performed in a case where there is an end instruction, it is possible to prevent the display of the tomographic image being ended even though there is an unreferenced detection result. Accordingly, in a case where the plurality of tomographic images including the detection result of the abnormal part are displayed, it is possible to reliably prevent overlooking the abnormality.

Figure 11:
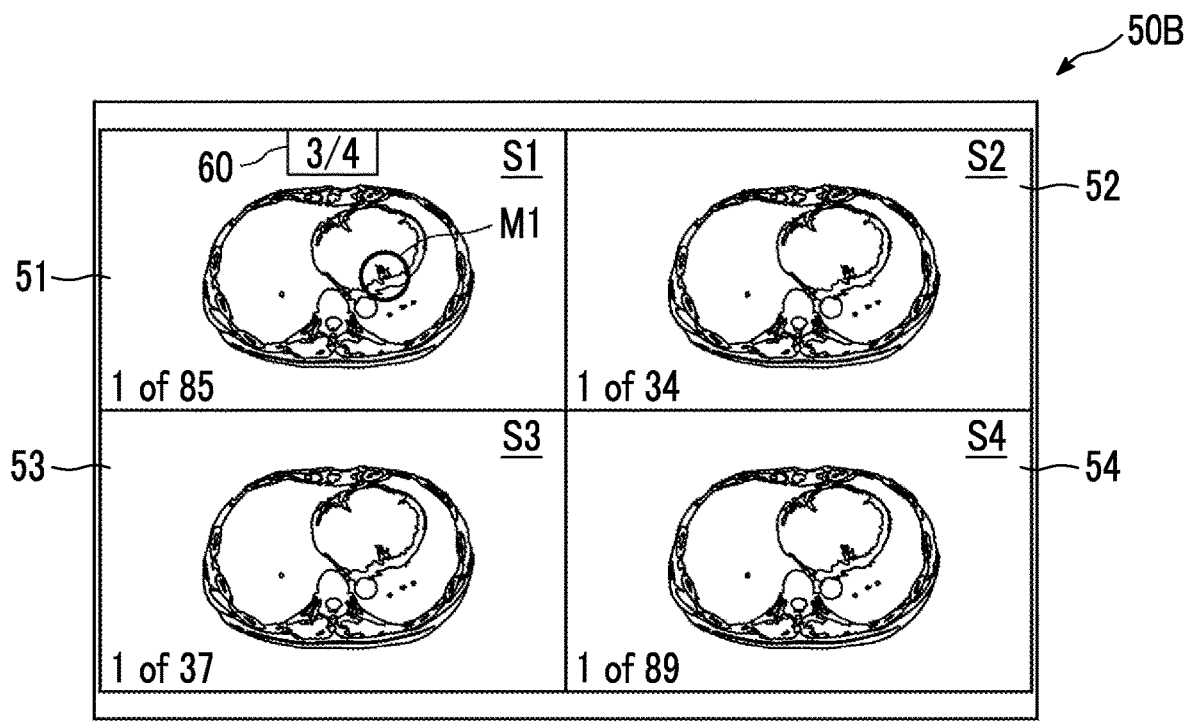
FIG. 11 is a diagram illustrating another display screen in a detection result display mode.

In the above embodiment, the number of referenced detection results is used as the reference information, but the invention is not limited thereto. The number of unreferenced detection results may be used as the reference information. In this case, in a state where the leading image is displayed on the display screen 50B in the detection result display mode as illustrated in FIG. 8, in the imaging series S1, the number of referenced detection results is 1, and the number of unreferenced detection results is 3. Therefore, in the state display area 60, "3/4" is displayed as illustrated in FIG. 11.

Further, in the above embodiment, during the detection result display mode, the images including the detection result can be sequentially displayed. In this case, the operator gives an instruction to sequentially display the images including the detection result, by using the input unit 15. Accordingly, the first display controller 21 sequentially displays the tomographic images to which the detection result is added, in the image display area 51. For example, as illustrated in FIG. 8, in a state where the leading image of the imaging series S1 to which the detection result is added is displayed in the image display area 51, in a case where the operator gives an instruction to sequentially display the images including the detection result, by using the input unit 15, the tomographic image to which the second detection result is added is displayed as illustrated in FIG. 9.

Figure 12:
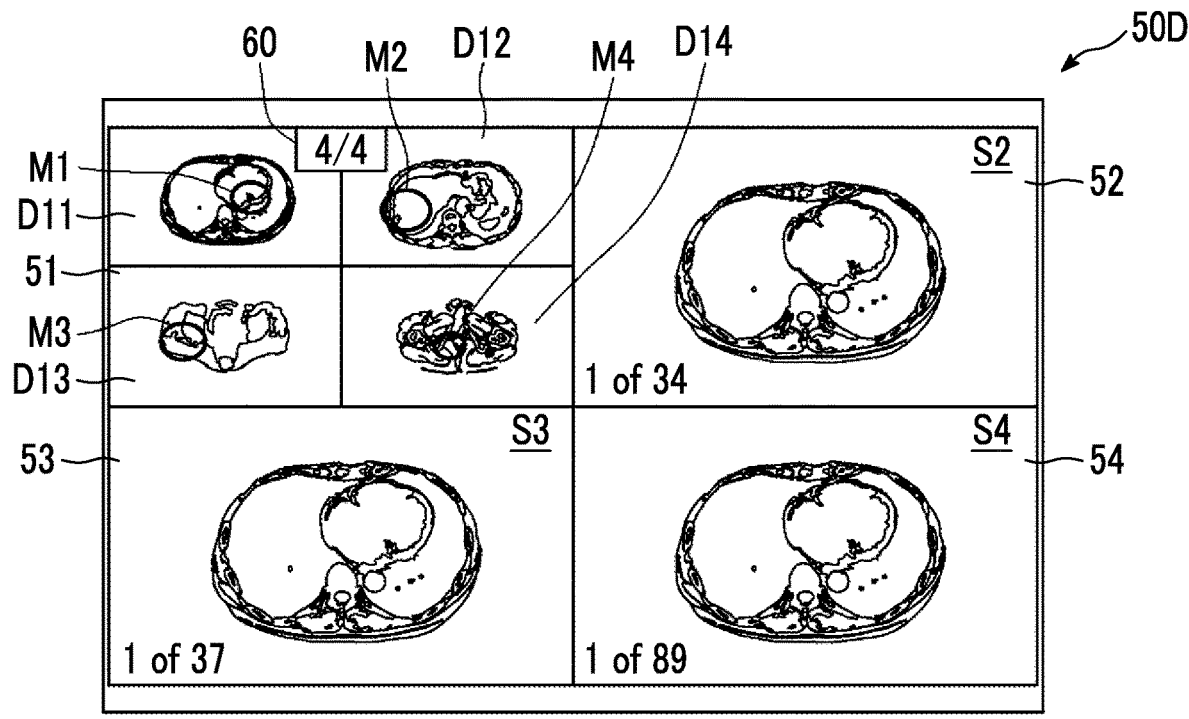
FIG. 12 is a diagram illustrating a display screen in which tomographic images including a detection result are displayed in parallel.

Further, in the above embodiment, during the detection result display mode, the images including the detection result can be displayed in parallel. In this case, the operator gives an instruction to display the images including the detection result in parallel, by using the input unit 15. Accordingly, the first display controller 21 displays all of the tomographic images to which the detection result is added, in parallel in the image display area 51. FIG. 12 is a diagram illustrating a display screen in which tomographic images including the detection result are displayed in parallel. As illustrated in FIG. 12, in the image display area 51 of a display screen 50D, four tomographic images D11 to D14 to which marks M1 to M4 representing the detection result are respectively added are displayed in parallel. In a case where the images including the detection result are displayed in parallel in this manner, the number of referenced detection results is 4. Accordingly, in the state display area 60 in the image display area 51 of the display screen 50D, "4/4" is displayed.

Figure 13:
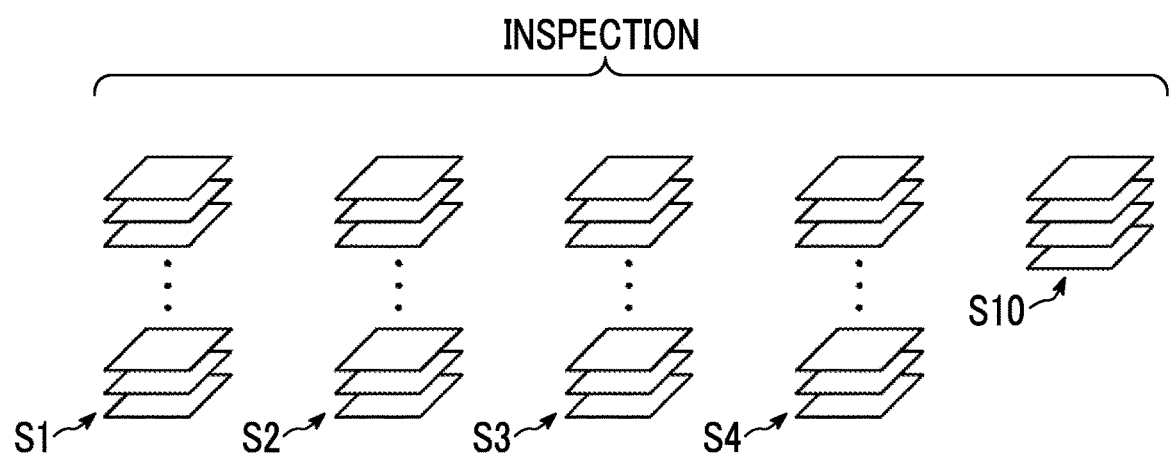
FIG. 13 is a diagram for describing an imaging series.

Further, in the above embodiment, the tomographic images including the imaging series to which the detection result is added are acquired as the medical images to be acquired for the inspection, but the invention is not limited thereto. For example, as illustrated in FIG. 13, an imaging series S10 including the detection result image representing the detection result separate from the tomographic images of the imaging series S1 to S4 may be stored in the image storage server 3. In this case, in the detection result display mode, the detection result image included in the imaging series S10 is superimposed and displayed on the tomographic image including the abnormal part such as a lesion among the tomographic images of the imaging series S 1. Accordingly, similar to the image including the detection result in the above embodiment, the tomographic image to which the mark is added is displayed.

Figure 14:
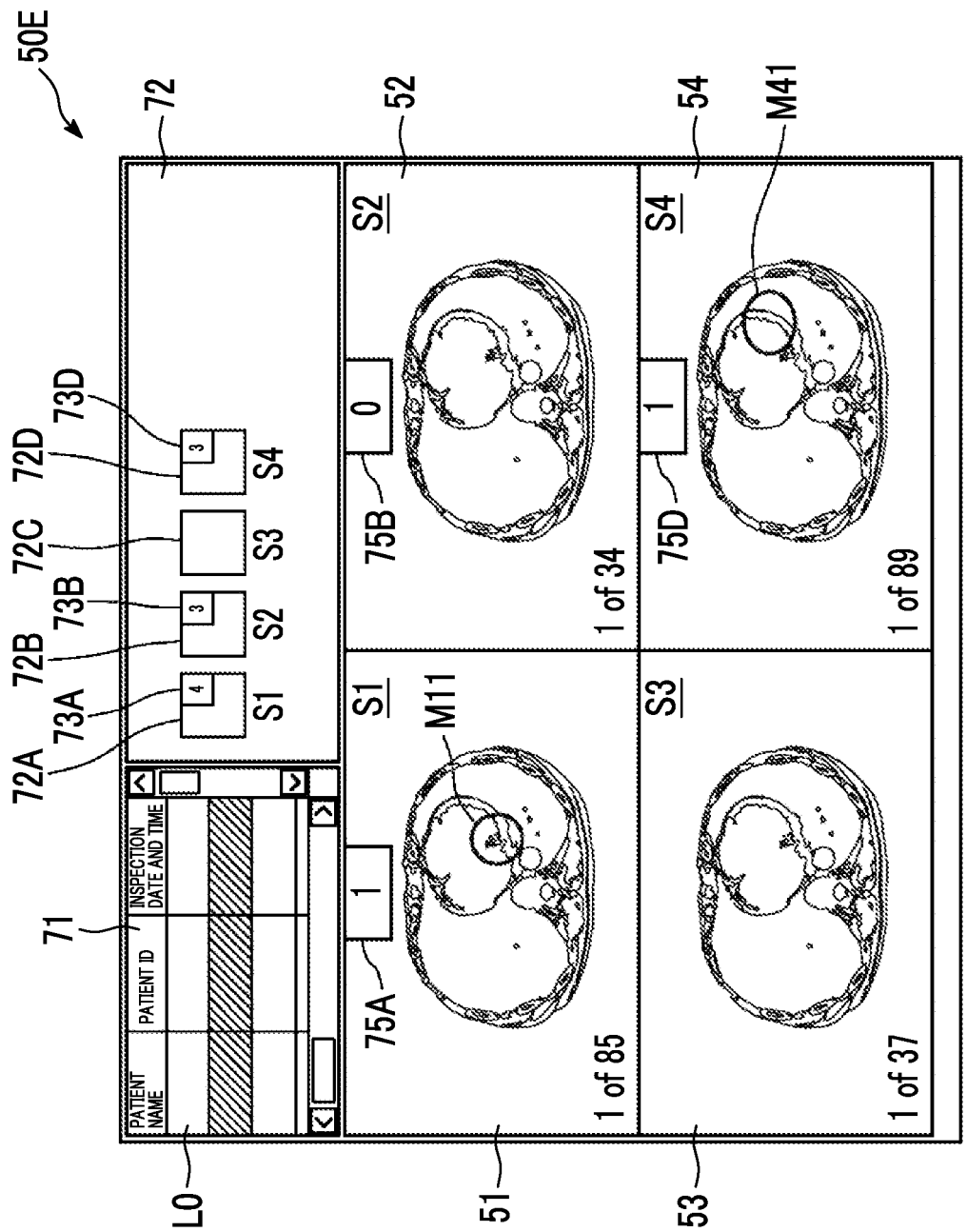
FIG. 14 is a diagram illustrating another display state of a total number of detection results and reference information.

Further, in the above embodiment, both the total number of detection results and the reference information are displayed in the state display area 60, but the invention is not limited thereto. FIG. 14 is a diagram illustrating another display state of the total number of detection results and the reference information. As illustrated in FIG. 14, a display screen 50E includes an inspection list display area 71 where the inspection list LO is displayed, and a thumbnail display area 72 in which thumbnail images of the four imaging series S1 to S4 are displayed, in addition to the four image display areas 51 to 54. Here, it is assumed that four detection results are included in the imaging series S 1, three detection results are included in the imaging series S2, no detection result is included in the imaging series S3, and three detection results are included in the imaging series S4.

The inspection list LO illustrated in FIG. 4 is displayed in the inspection list display area 71. Thumbnail images 72A to 72D that are the representative pictures of the imaging series S1 to S4 are displayed in the thumbnail display area 72. As the representative picture, for example, the leading image among the tomographic images included in the imaging series S1 to S4 or the tomographic image including the abnormal part first viewed from the leading image can be used. In the thumbnail images 72A, 72B, and 72D displayed in the thumbnail display area 72, total number display areas 73A, 73B, and 73D where the total number of detection results is displayed are added.

As illustrated in FIG. 14, "4" is displayed in the total number display area 73A for the imaging series S1, "3" is displayed in the total number display area 73B for the imaging series S2, and "3" is displayed in the total number display area 73D for the imaging series S4. These represent that the imaging series S1 includes four detection results, the imaging series S2 includes three detection results, the imaging series S3 does not include a detection result, and the imaging series S4 includes three detection results. A total number display area may be displayed in the thumbnail image 72C of the imaging series S3. In this case, "0" is displayed in the total number display area.

Further, marks M11 and M41 representing the detection result are respectively added to the tomographic images (here, leading images) being displayed in the image display areas 51 and 54. Further, reference information display areas 75A, 75B, and 75D where the reference information is displayed are respectively displayed in the image display areas 51, 52, and 54. In FIG. 14, "1" is displayed in the reference information display area 75A for the imaging series S1, "0" is displayed in the reference information display area 75B for the imaging series S2, and "1" is displayed in the reference information display area 75D for the imaging series S4. These represent that the number of detection results referenced in the imaging series S1 is 1, the number of detection results referenced in the imaging series S2 is 0, and the number of detection results referenced in the imaging series S4 is 1.

Also in the embodiment illustrated in FIG. 14, the number of unreferenced detection results may be used as the reference information. In this case, "3" is displayed in the reference information display area 75A for the imaging series S1 illustrated in FIG. 14, "3" is displayed in the reference information display area 75B for the imaging series S2, and "2" is displayed in the reference information display area 75D for the imaging series S4.

Figure 15:
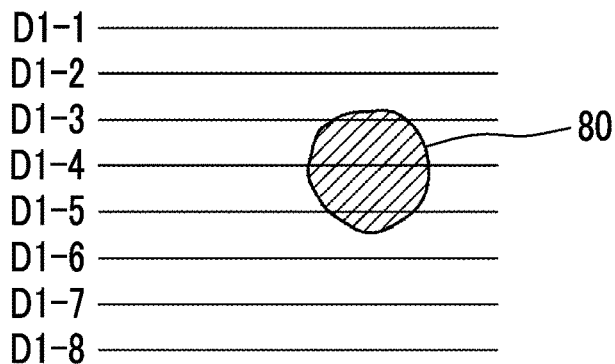
FIG. 15 is a diagram for describing tomographic images including an abnormal part.
Figure 16:
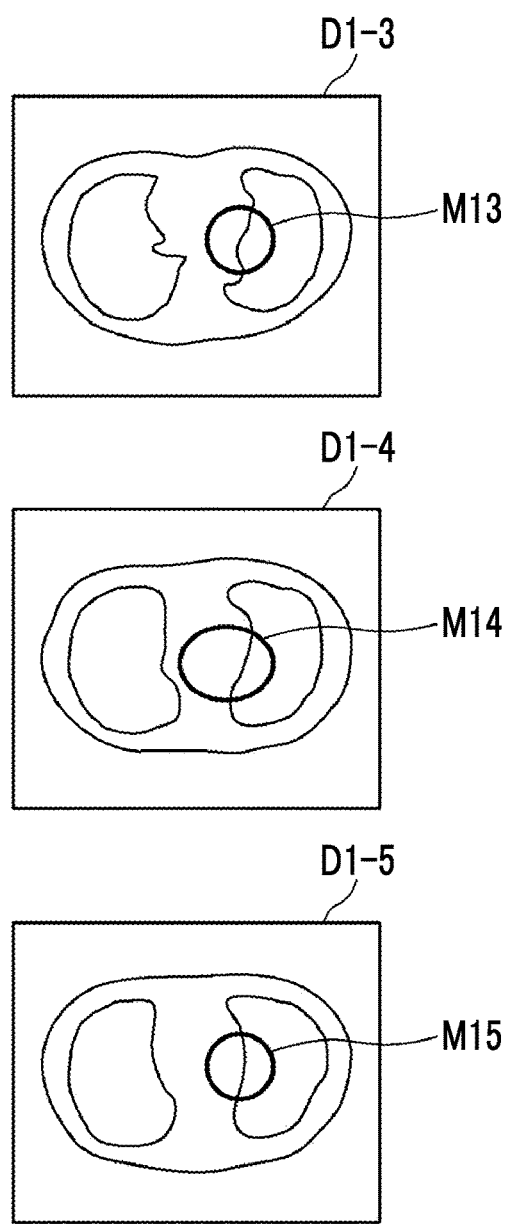
FIG. 16 is a diagram for describing tomographic images including an abnormal part.

However, the abnormal part included in the subject has three-dimensional spread in the subject. Therefore, in the three-dimensional image such as the CT image or the MRI image, the abnormal part is present across the plurality of tomographic images. FIG. 15 is a diagram illustrating an abnormal part present across the plurality of tomographic images. In FIG. 15, 8 tomographic images D1-1 to D1-8 are displayed for the description. As illustrated in FIG. 15, an abnormal part 80 is present across the three tomographic images D1-3 to D1-5 among the tomographic images D1-1 to D1-8. In this case, marks M13 to M15 representing the detection result are added to the three tomographic images D1-3 to D1-5 as illustrated in FIG. 16.

During the analysis process of the CAD, there is a case where the analysis is two-dimensionally performed on each of the tomographic images included in the imaging series, and a case where the analysis is three-dimensionally performed on the three-dimensional image consisting of all of the tomographic images included in the imaging series. In the situation illustrated in FIG. 15, in a case where the analysis is two-dimensionally performed, the total number of detection results is 3. On the other hand, in a case where the analysis is three-dimensionally performed, the total number of detection results is 1, but the number of tomographic images including the detection result is 3.

In the embodiment, in a case where the analysis is three-dimensionally performed, as the total number of detection results, the number of detected abnormal parts may be used or the number of tomographic images including the abnormal part may be used. For example, in a case where the abnormal part is detected as illustrated in FIGS. 15 and 16, the total number of detection results may be 1 or 3.

In a case where the number of abnormal parts is used as the total number of detection results, a case where some tomographic images among the plurality of tomographic images including the detection result are referenced may be treated as all of the detection results being referenced. For example, in a case where the abnormal part is detected as illustrated in FIGS. 15 and 16, the total number of detection results is 1, and in a case where any one tomographic image among the three tomographic images D1-3 to D1-5 is referenced, the reference information may be 1 (in a case where the reference information is the number of referenced detection results). In a case where the reference information is the number of unreferenced detection results, the reference information may be 0. In addition, in a case where the number of abnormal parts is used as the total number of detection results, a case where all of the tomographic images including the detection result are referenced may be treated as all of the detection results being referenced. For example, in a case where the abnormal part is detected as illustrated in FIGS. 15 and 16, the total number of detection results is 1, and in a case where all of the three tomographic images D1-3 to D1-5 are referenced, the reference information may be 1 (in a case where the reference information is the number of referenced detection results). In a case where the reference information is the number of unreferenced detection results, the reference information may be 0.

In a case where the number of tomographic images including the abnormal part is used as the total number of detection results, the number of referenced tomographic images among the plurality of tomographic images including the detection result may be treated as the number of referenced detection results. For example, in a case where the abnormal part is detected as illustrated in FIGS. 15 and 16, the total number of detection results is 3, and in a case where any one tomographic image among the three tomographic images D1-3 to D1-5 is referenced, the reference information may be 1 (in a case where the reference information is the number of referenced detection results). In a case where the reference information is the number of unreferenced detection results, the reference information may be 2. In this case, in a case where all of the detection results are referenced, the reference information is 3 in a case where the reference information is the number of referenced detection results, and the reference information is 0 in a case where the reference information is the number of unreferenced detection results. In addition, in a case where the number of tomographic images including the abnormal part is used as the total number of detection results, a case where some tomographic images among the plurality of tomographic images including the detection result are referenced may be treated as all of the detection results being referenced. For example, in a case where the abnormal part is detected as illustrated in FIGS. 15 and 16, the total number of detection results is 3, and in a case where all of the three tomographic images D1-3 to D1-5 are referenced, the reference information may be 3 (in a case where the reference information is the number of referenced detection results). In a case where the reference information is the number of unreferenced detection results, the reference information may be 0.

Figure 17:
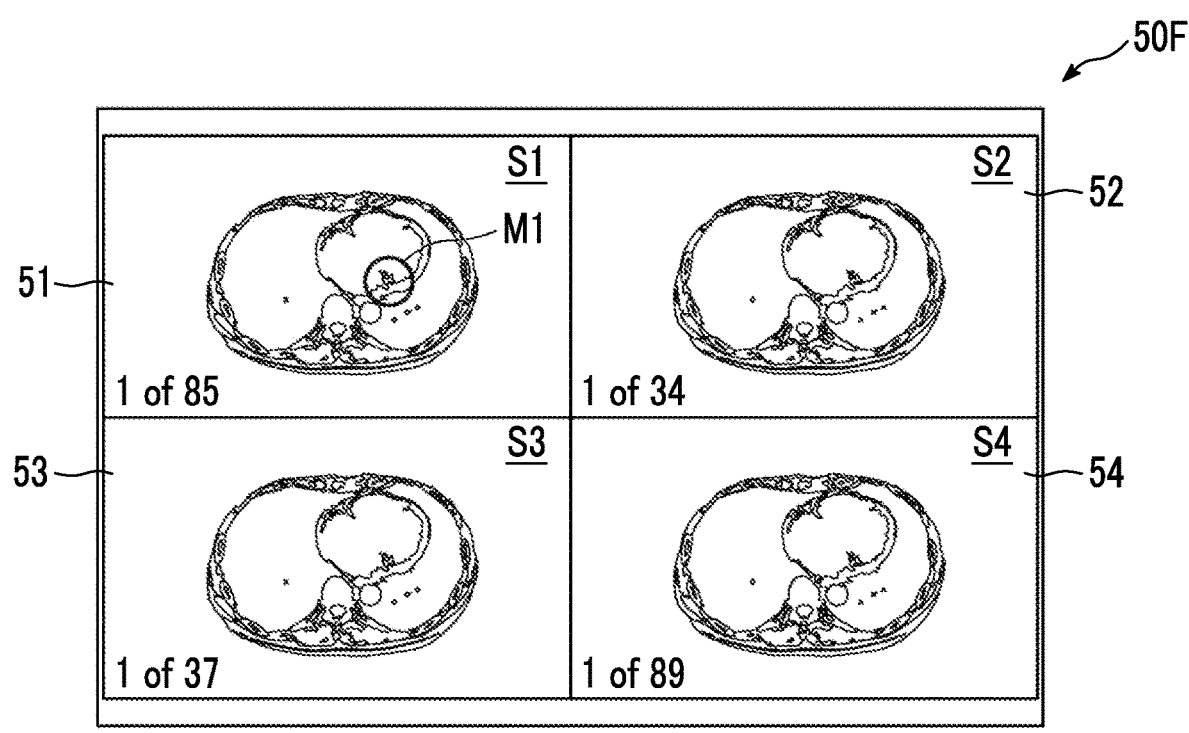
FIG. 17 is a diagram illustrating another display screen in a detection result display mode.

In the embodiment of the display screen 50B illustrated in FIG. 8, in the detection result non-display mode, the display and non-display of the state display area 60, that is, the total number of detection results and the reference state, may be switched by the instruction from the input unit 15. For example, on the display screen 50B illustrated in FIG. 8, in a case where the operator gives an instruction for the non-display of the state display area 60 by using the input unit 15, the state display area 60 is not displayed in the image display area 51 as illustrated on a display screen 50F of FIG. 17. In this case, in the state display area 60, only the total number of detection results may be displayed or only the reference state may be displayed.

Figure 18:
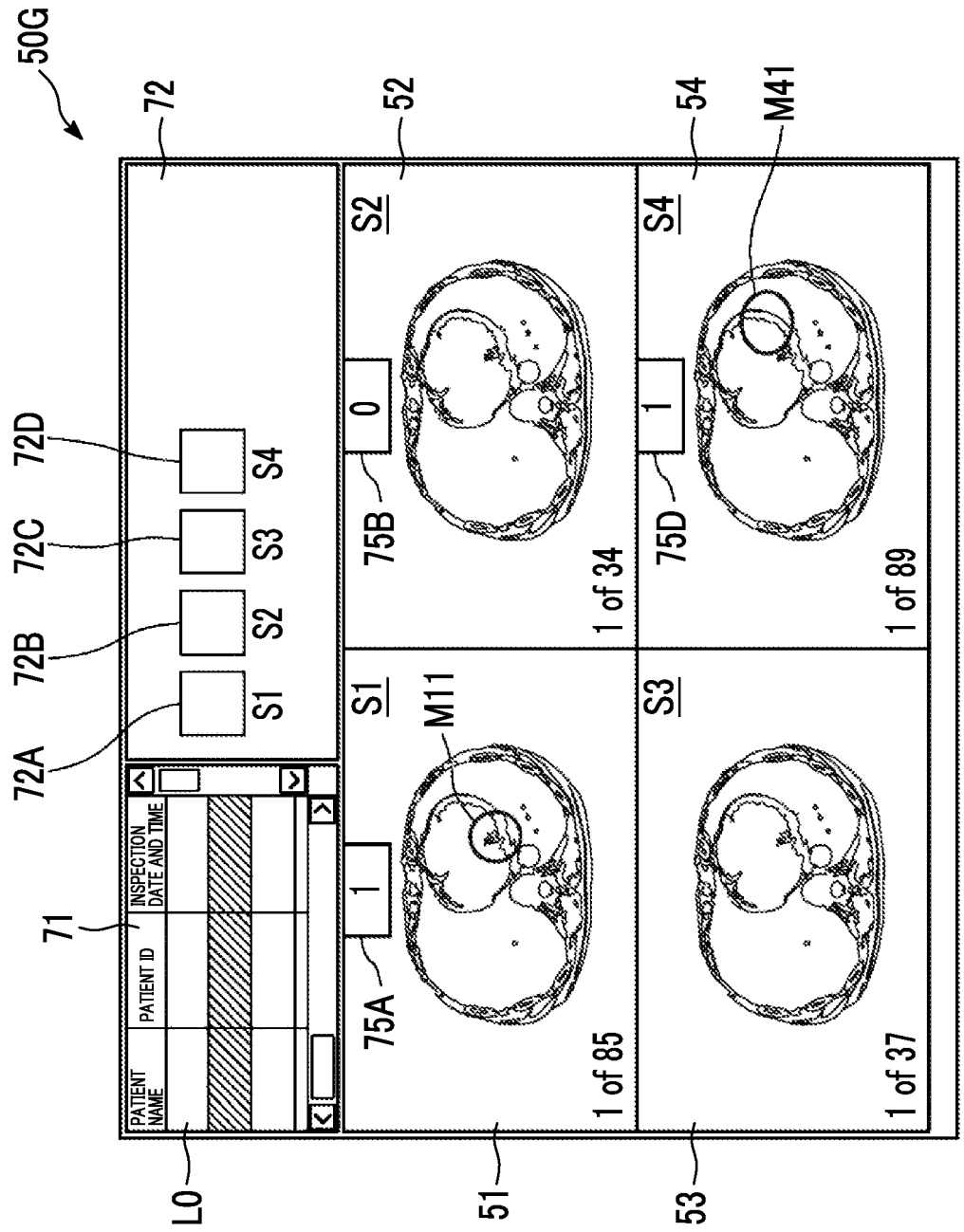
FIG. 18 is a diagram illustrating another display screen in a detection result display mode.
Figure 19:
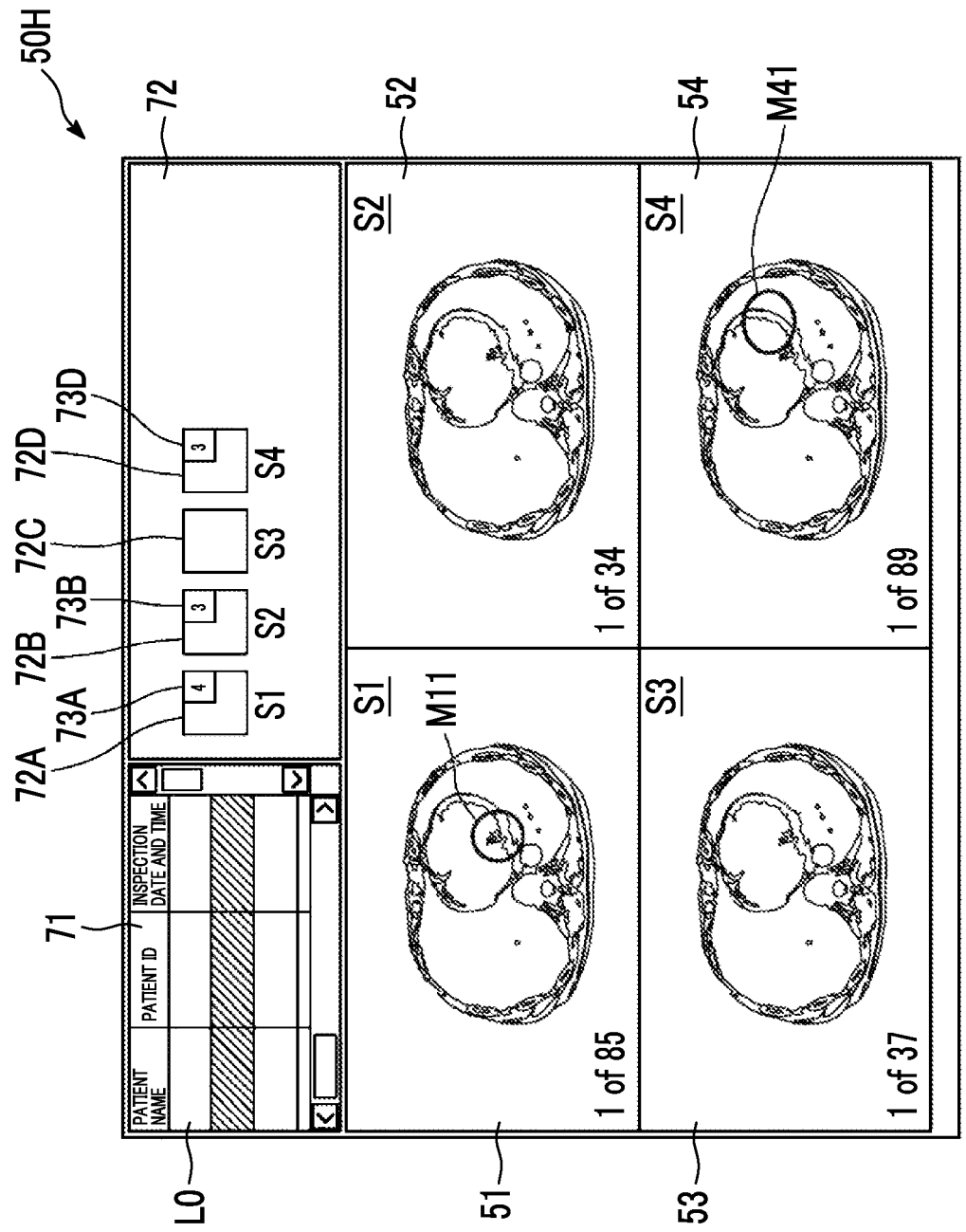
FIG. 19 is a diagram illustrating another display screen in a detection result display mode.

In the embodiment of the display screen 50E illustrated in FIG. 14, the display and non-display of at least one of the total number display areas 73A, 73B, and 73D or the reference information display areas 75A, 75B, and 75D may be switched by the instruction from the input unit 15. For example, on the display screen 50E illustrated in FIG. 14, in a case where the operator gives an instruction for the non-display of the total number display areas 73A, 73B, and 73D by using the input unit 15, the total number display areas 73A, 73B, and 73D are not displayed in the thumbnail images 72A to 72D of the thumbnail display area 72 as illustrated on a display screen 50G of FIG. 18. For example, on the display screen 50E illustrated in FIG. 14, in a case where the operator gives an instruction for the non-display of the reference information display areas 75A, 75B, and 75D by using the input unit 15, the reference information display areas 75A, 75B, and 75D are not displayed in the image display areas 51, 52, and 54 as illustrated on a display screen 50H of FIG. 19. Both the total number display areas 73A, 73B, and 73D and the reference information display areas 75A, 75B, and 75D may not be displayed.

Figure 20:
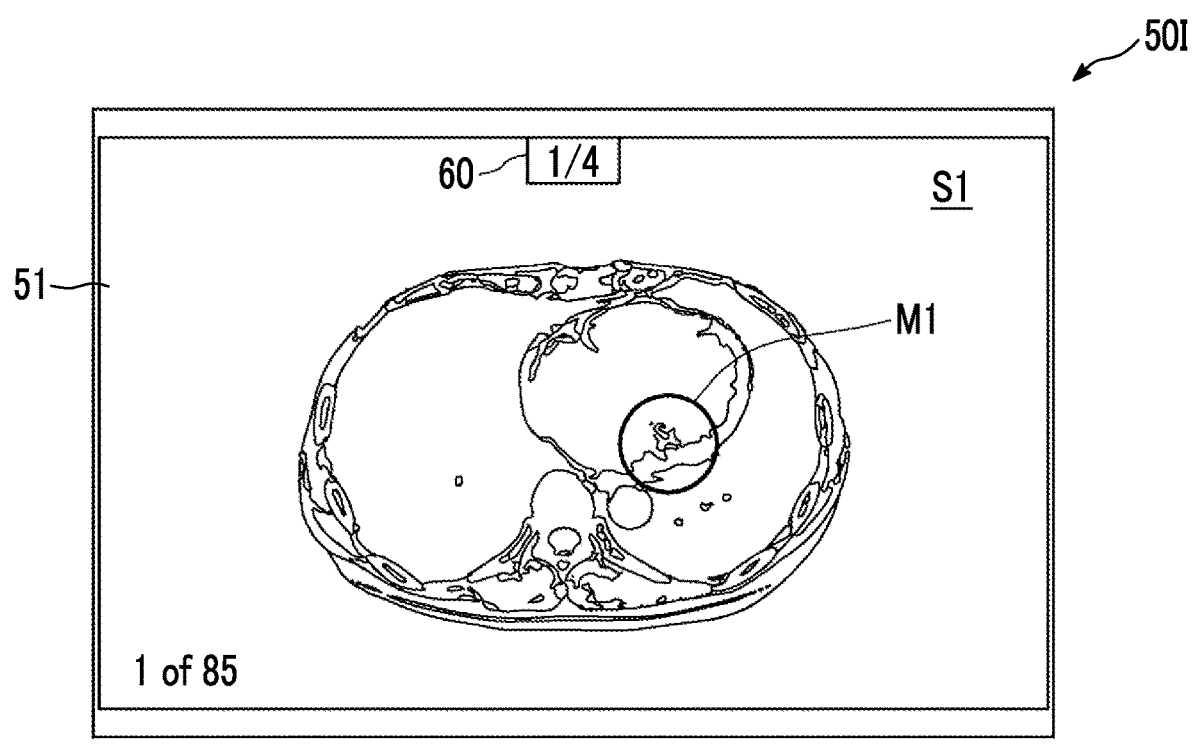
FIG. 20 is a diagram illustrating a display screen in which only an imaging series including an inspection result is displayed.

Further, in the above embodiment, as illustrated in FIG. 20, a display screen 50I including only the imaging series S1 to which the detection result is added may be displayed.

Further, in the above embodiment, the medical image display device 1 comprises the notification unit 24, but the invention is not limited thereto. The medical image display device 1 may be configured to not comprise the notification unit 24.

Further, in the above embodiment, for example, the following various processors can be used as the hardware structure of processing units executing various processes such as the image acquisition unit 20, the first display controller 21, the second display controller 22, the third display controller 23, and the notification unit 24. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (programs) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

As an example where a plurality of processing units are configured by one processor, first, there is a form where one processor is configured by a combination of one or more CPUs and software as typified by a computer, such as a client and a server, and this processor functions as a plurality of processing units. Second, there is a form where a processor fulfilling the functions of the entire system including a plurality of processing units by means of one integrated circuit (IC) chip as typified by a system on chip (SoC) or the like is used. In this manner, various processing units are configured by using one or more of the above-described various processors as hardware structures.

In addition, specifically, an electric circuit (circuitry) obtained by combining circuit elements, such as semiconductor elements, can be used as the hardware structure of the various processors.

What is claimed is:

1. A medical image display device comprising at least one processor, wherein the processor is configured to:
    display in a first display area, an annotated medical image in which a detection result of at least one abnormal part is added to a position of the at least one abnormal part in the annotated medical image containing the at least one abnormal part, on a display, wherein the annotated medical image belongs to a first series of medical images in the first display area;
    display, further in the first display area, a first page number corresponding to the annotated medical image representing a first position of the annotated medical image within the first series of the medical images and a first total number of the first series of medical images;
    display, further in the first display area, a second total number of detection results of the first series of the medical images containing the at least one abnormal part; and
    display further in the first display area, a second page number representing a second position of the annotated medical image within the second total number of detection results of the first series of the medical images containing the at least one abnormal part, wherein the first series of medical images comprises the at least one medical image containing the at least one abnormal part and other medical image which does not contain the at least one abnormal part.

2. The medical image display device according to claim 1, wherein the second total number of detection results includes a number of referenced detection results among the first series of medical images.

3. The medical image display device according to claim 1, wherein the second total number of detection results includes a number of unreferenced detection results among the first series of medical image.

4. The medical image display device according to claim 3, wherein the number of unreferenced detection results is displayed in response to having been detected, and the processor is further configured to display a warning message in response to having detected the unreferenced detection results.

5. The medical image display device according to claim 1, wherein the processor is configured to, in a case where there is at least one unreferenced detection result at the time of ending display of the first series of medical images, give a notification that there is the unreferenced detection result.

6. The medical image display device according to claim 1, wherein the processor is configured to switch between display and non-display of the second page number and the second total number of detection results.

7. The medical image display device according to claim 1, wherein the processor is configured to switch between display and non-display of reference information.

8. The medical image display device according to claim 1, wherein the processor is configured to display only the annotated medical image to which a detection result is added.

9. The medical image display device according to claim 8, wherein in a case where a detection result is added to each of a plurality of medical images of the first series of medical images, the processor is configured to sequentially display each of the plurality of medical images to which the detection result is added.

10. The medical image display device according to claim 8, wherein in a case where a detection result is added to each of a plurality of medical images of the first series of medical images, the processor is configured to display each of the plurality of medical images to which the detection result is added, in parallel.

11. The medical image display device according to claim 1,
wherein the first series of medical images are displayed among a plurality of series of medical images for one inspection.

12. The medical image display device according to claim 1, wherein the processor is configured to acquire, as a detection result, information on a center position of the at least one abnormal part and a diameter of the at least one abnormal part.

13. The medical image display device according to claim 1, wherein the first series of medical images comprises the at least one abnormal part and a normal part.

14. The medical image display device according to claim 1, wherein the medical image display device further displays a second display area which displays a medical image of a second series of medical images, a third page number of the medical image, and a third total page number of the second series of medical images.

15. The medical image display device according to claim 14, wherein the second page number and the second total number of detection results only refer to annotated medical images in the first series of medical images and not annotated medical images in the second series of medical images.

16. A medical image display method comprising:
displaying in a first display area, an annotated medical image in which a detection result of at least one abnormal part is added to a position of the at least one abnormal part in the annotated medical image containing the at least one abnormal part, on a display, wherein the annotated medical image belongs to a first series of medical images in the first display area;
displaying, further in the first display area, a first page number corresponding to the annotated medical image representing a first position of the annotated medical image within the first series of the medical images and a first total number of the first series of medical images;
displaying, further in the first display area, a second total number of detection results of the at least one medical image containing the at least one abnormal part; and
displaying, further in the first display area, a second page number representing a second position of the annotated medical image within the second total number of detection results of the at least one medical image containing the at least one abnormal part, wherein the first series of medical images comprises the at least one medical image containing the at least one abnormal part and another medical image which does not contain the at least one abnormal part.

17. A non-transitory computer-readable storage medium that stores a medical image display program causing a computer to execute:
displaying in a first display area, an annotated medical image in which a detection result of at least one abnormal part is added to a position of the at least one abnormal part in the annotated medical image containing the at least one abnormal part, on a display, wherein the annotated medical image belongs to a first series of medical images in the first display area;
displaying, further in the first display area, a first page number corresponding to the annotated medical image representing a first position of the annotated medical image within the first series of the medical images and a first total number of the first series of medical images;
displaying, further in the first display area, a second total number of detection results of the at least one medical image containing the at least one abnormal part; and
displaying, further in the first display area, a second page number representing a second position of the annotated medical image within the second total number of detection results of the at least one medical image containing the at least one abnormal part, wherein the first series of medical images comprises the at least one medical image containing the at least one abnormal part and another medical image which does not contain the at least one abnormal part.

\* \* \* \* \*